(12) United States Patent
Haecker et al.

(10) Patent No.: US 9,943,634 B2
(45) Date of Patent: Apr. 17, 2018

(54) DEVICE FOR CONNECTING MULTI-FUNCTIONAL DISPOSABLE CASSETTE TO EXTRACORPOREAL BLOOD TREATMENT APPARATUS

(75) Inventors: Juergen Haecker, Neu-Anspach (DE); Uwe Lapp, Butzbach (DE); Udo Waeber, Offenbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 727 days.

(21) Appl. No.: 13/255,286

(22) PCT Filed: Mar. 9, 2010

(86) PCT No.: PCT/EP2010/001464
§ 371 (c)(1),
(2), (4) Date: Oct. 26, 2011

(87) PCT Pub. No.: WO2010/102790
PCT Pub. Date: Sep. 16, 2010

(65) Prior Publication Data
US 2012/0030921 A1 Feb. 9, 2012

(30) Foreign Application Priority Data
Mar. 10, 2009 (DE) .................. 10 2009 012 633

(51) Int. Cl.
*A61M 1/14* (2006.01)
*A61M 1/36* (2006.01)

(52) U.S. Cl.
CPC ............ *A61M 1/3621* (2013.01); *A61M 1/14* (2013.01); *A61M 2205/12* (2013.01);
(Continued)

(58) Field of Classification Search
CPC .. A61M 1/14; A61M 1/3621; A61M 2205/12; A61M 2205/127;
(Continued)

(56) References Cited

U.S. PATENT DOCUMENTS

| 4,137,913 A | 2/1979 | Georgi |
| 4,273,121 A | 6/1981 | Jassawalla |

(Continued)

FOREIGN PATENT DOCUMENTS

| CN | 1321105 | 11/2001 |
| CN | 1321105 A | 11/2001 |

(Continued)

OTHER PUBLICATIONS

PCT International Search Report for PCT/EP2010/001464, dated Feb. 22, 2012.
(Continued)

*Primary Examiner* — Jermie Cozart
(74) *Attorney, Agent, or Firm* — Fish & Richardson P.C.

(57) ABSTRACT

The present invention relates to a device for connecting at least one external functional device to an arrangement, wherein the device includes at least one first contact portion and at least one second contact portion for receiving the external functional device between the first contact portion and the second contact portion, and at least the first contact portion or the second contact portion is movable. It further relates to a method for connecting at least one external functional device to an arrangement by using the device of the present invention, as well as an arrangement which includes at least one device of the present invention.

19 Claims, 2 Drawing Sheets

(52) U.S. Cl.
CPC .. *A61M 2205/127* (2013.01); *Y10T 29/49826* (2015.01); *Y10T 403/32* (2015.01); *Y10T 403/32254* (2015.01); *Y10T 403/32631* (2015.01); *Y10T 403/32975* (2015.01)

(58) Field of Classification Search
CPC ..... Y10T 403/32975; Y10T 403/32254; Y10T 403/32631; Y10T 403/32; Y10T 29/49826
USPC ....... 29/428, 700; 604/28, 29, 42; 417/477.2
See application file for complete search history.

(56) References Cited

U.S. PATENT DOCUMENTS

| | | | |
|---|---|---|---|
| 4,322,201 A | 3/1982 | Archibald | |
| 4,410,322 A | 10/1983 | Archibald | |
| 4,474,309 A | 10/1984 | Solomon | |
| 4,585,442 A * | 4/1986 | Mannes | 604/250 |
| 4,639,245 A | 1/1987 | Pastrone et al. | |
| 4,657,490 A | 4/1987 | Abbott | |
| 4,696,671 A | 9/1987 | Epstein et al. | |
| 4,818,186 A | 4/1989 | Pastrone et al. | |
| 4,842,584 A | 6/1989 | Pastrone | |
| 5,002,471 A | 3/1991 | Perlov | |
| 5,313,992 A | 5/1994 | Grabenkort | |
| 5,350,357 A | 9/1994 | Kamen et al. | |
| 5,415,528 A | 5/1995 | Ogden et al. | |
| 5,938,634 A | 8/1999 | Packard | |
| 6,315,707 B1 | 11/2001 | Smith et al. | |
| 6,542,761 B1 | 4/2003 | Jahn et al. | |
| 6,645,166 B2 | 11/2003 | Scheunert et al. | |
| 6,752,172 B2 | 6/2004 | Lauer | |
| 6,821,432 B2 | 11/2004 | Metzner | |
| 7,044,432 B2 | 5/2006 | Beden et al. | |
| 7,153,286 B2 | 12/2006 | Busby et al. | |
| 7,503,915 B2 | 3/2009 | Beden et al. | |
| 7,648,627 B2 | 1/2010 | Beden et al. | |
| 7,789,849 B2 * | 9/2010 | Busby et al. | 604/29 |
| 7,959,196 B2 | 6/2011 | Dale | |
| 7,988,686 B2 | 8/2011 | Beden et al. | |
| 8,105,266 B2 * | 1/2012 | Childers et al. | 604/6.16 |
| 8,142,653 B2 | 3/2012 | Beden et al. | |
| 8,210,049 B2 | 7/2012 | Brugger | |
| 8,366,921 B2 | 2/2013 | Beden et al. | |
| 8,377,293 B2 | 2/2013 | Beden et al. | |
| 8,388,582 B2 * | 3/2013 | Eubanks et al. | 604/239 |
| 8,435,408 B2 | 5/2013 | Beden et al. | |
| 2003/0100882 A1 | 5/2003 | Beden et al. | |
| 2005/0095152 A1* | 5/2005 | Dale | 417/477.2 |
| 2005/0126998 A1 | 6/2005 | Childers | |
| 2006/0079826 A1 | 4/2006 | Beden et al. | |
| 2007/0112297 A1* | 5/2007 | Plahey et al. | 604/28 |
| 2007/0213654 A1 | 9/2007 | Lundtveit et al. | |
| 2007/0276328 A1 | 11/2007 | Childers et al. | |
| 2009/0012448 A1* | 1/2009 | Childers et al. | 604/29 |
| 2009/0299271 A1* | 12/2009 | Zhang et al. | 604/29 |
| 2009/0299272 A1* | 12/2009 | Hopping et al. | 604/29 |
| 2010/0133153 A1 | 6/2010 | Beden et al. | |
| 2011/0239742 A1 | 10/2011 | Müller et al. | |
| 2012/0181225 A1 | 7/2012 | Weis | |
| 2012/0181226 A1 | 7/2012 | Lauer | |
| 2013/0118961 A1 | 5/2013 | Beden et al. | |
| 2013/0118970 A1 | 5/2013 | Beden et al. | |

FOREIGN PATENT DOCUMENTS

| | | |
|---|---|---|
| CN | 1340443 | 3/2002 |
| CN | 1340443 A | 3/2002 |
| DE | 1226740 | 10/1966 |
| DE | 19837667 | 3/2000 |
| DE | 10034711 | 2/2002 |
| DE | 10039196 | 2/2002 |
| DE | 10042324 | 2/2002 |
| DE | 10053441 | 5/2002 |
| DE | 102 24 750 A1 | 12/2003 |
| DE | 10224750 | 12/2003 |
| DE | 603 18 044 T2 | 12/2008 |
| DE | 60318044 | 12/2008 |
| DE | 10 2007 042 964.0 A1 | 3/2009 |
| DE | 10 2007 042 964 A1 | 3/2009 |
| DE | 102007042964 | 3/2009 |
| DE | 10 2009 012 632.5 A1 | 9/2010 |
| DE | 10 2009 012 632 A1 | 9/2010 |
| DE | 102009012632 | 9/2010 |
| EP | 0410125 | 8/1993 |
| JP | 59-149189 | 8/1984 |
| JP | 3096850 | 10/1991 |
| JP | 200121884 | 1/2001 |
| JP | 2001218841 | 8/2001 |
| JP | 2001218841 A | 8/2001 |
| JP | 3355176 | 12/2002 |
| JP | 2003-508180 | 3/2003 |
| JP | 2003508180 T | 3/2003 |
| JP | 2003508183 | 3/2003 |
| JP | 2010538687 | 12/2010 |
| WO | 9822167 | 5/1998 |
| WO | 01/17653 A1 | 3/2001 |
| WO | 01/017653 A1 | 3/2001 |
| WO | 01/018396 A1 | 3/2001 |
| WO | 0117653 | 3/2001 |
| WO | 0118396 | 3/2001 |
| WO | 0225146 | 3/2002 |
| WO | 2007-0140241 A1 | 12/2007 |
| WO | 20070140241 | 12/2007 |
| WO | 2010/066441 A1 | 6/2010 |
| WO | 2010066441 | 6/2010 |
| WO | 2010/102784 A1 | 9/2010 |
| WO | 2012161744 | 11/2012 |

OTHER PUBLICATIONS

Ronco et al., "Evolution of Machines for Automated Peritoneal Dialysis," Technical Aspects and Solutions for APD, 1999, 129:142-161, 20 pages.

International Search Report in International Application No. PCT/EP2010/001464, dated Feb. 22, 2012, 2 pages (with English translation).

* cited by examiner

US 9,943,634 B2

DEVICE FOR CONNECTING MULTI-FUNCTIONAL DISPOSABLE CASSETTE TO EXTRACORPOREAL BLOOD TREATMENT APPARATUS

CROSS REFERENCE TO RELATED APPLICATIONS

This is a 371 national phase application of PCT/EP2010/001464 filed Mar. 9, 2010, claiming priority to German Patent Application No. 10 2009 012 633.3 filed Mar. 10, 2009.

FIELD OF INVENTION

The present invention relates to a device for connecting at least one external functional device to an arrangement. It further relates to a method for connecting at least one external functional device to an arrangement by using the device of the present invention, and an arrangement which includes a device of the present invention.

BACKGROUND OF THE INVENTION

In technical arrangements such as, e.g., treatment machines of medical technology, laboratory technological arrangements, or also arrangements for the food production, functional coupling of external functional device to the arrangement is frequently envisaged. One example of such an external functional device is a disposable cassette as described in DE 10 2007 042 964.

Functional coupling of such external functional device usually requires their correct positioning and/or fixation on or at the arrangement in order to enable a proper co-operation of sensors and actuators on the side of the arrangement with the external functional device.

SUMMARY OF THE INVENTION

It is an object of the present invention to provide another device for connecting at least one external functional device to an arrangement. Moreover it is intended to specify a method for connecting at least one external functional device, as well as an arrangement including a like device.

The device of the present invention serves for connecting or for a connection, in particular coupling, of at least one external functional device to an arrangement and includes for this purpose at least one reception device having at least one first contact portion and at least one second contact portion between which the external functional device may be received. Here at least the first contact portion and/or the second contact portion is disposed, preferably mounted, so as to be movable. "Movable" is preferably understood to be an automatically adjusting movability or mobility of the movable contact portion.

Within the meaning of the present invention, however, a mobility such as, e.g., the mere pivoting movement about a suspension on a hinge such as, e.g., the well-known pivoting movement of a door, may be excluded by the expression "movable." Alternatively, on the other hand, this meaning may explicitly be encompassed by the present invention in connection with the expression "movable."

The first and/or the second contact portion may be provided such as to be disposed, preferably mounted, so as to be capable of oscillating, and thus at least be capable of oscillating in at least one direction at least during the connecting operation.

An "external functional device" as presently used may be a heat exchanger, a measurement device, a multi-functional disposable cassette, or the like.

An external functional device considered in accordance with the present invention may be suited for conducting medical fluids such as blood, substituate liquid, or the like. Such an external functional device may, for example, be a blood-conducting cassette. It may contain parts of an extracorporeal blood circulation. In particular it may be configured as a disposable cassette as described in DE 10 2007 042 964, the entire relevant disclosure of which is hereby incorporated by way of reference. In the context of the present disclosure it may be said that the expressions "may include", "may be" and the like are synonymous with the expressions "preferably includes", "preferably is" and the like, that are used here and elsewhere.

The external functional device may preferably transmit energy, measurement values and/or mechanical movements and forces to the arrangement or receive these from the latter, and may be in fluid communication with the arrangement. Alternatively it may, however, also only be retained by the arrangement while not interacting and/or being in signal communication and/or fluid communication therewith.

The external functional device to be received or connected may have a cover on at least one surface. Such a cover may be a film. The film may be provided for receiving sensors and/or actuators and/or conduits and/or parts thereof. The film may have openings for receiving such components, and/or such components may be integrated into the film and/or a laminate of films.

An "arrangement" within the meaning of the present invention may be a medical-technical arrangement such as, e.g., a blood treatment apparatus, for instance a dialysis apparatus, a hemodialysis apparatus, a hemodiafiltration apparatus or the like, an arrangement in laboratory technology, an arrangement in drug or food manufacture, or the like.

The expression "connecting" as presently used may denote or encompass a functional and/or mechanical connection of the external functional device to the arrangement.

The expression "coupling" as used herein may denote or encompass a functional and/or mechanical connection of the external functional device to a coupling mate on the side of the arrangement including, in the coupled condition of the external functional device, an interaction or signal communication or fluid communication between external functional device and arrangement.

A "coupling mate of the arrangement" may, for example, be a measurement device such as, e.g., a sensor. It may be configured as a fluid conduit and the like.

A "reception device" within the meaning of the present invention is a device that is suited for receiving at least one external functional device. Receiving may denote retaining, encircling, encompassing, covering of the external functional device and the like, as well as combinations thereof.

The "first contact portion" of the reception device is preferably provided on the device of the present invention itself or on an arrangement. It may be disposed inside the device or arrangement so as to be movable, e.g., oscillating in a vertical and/or horizontal or other direction relative to the center of the Earth.

The first contact portion may have various functions. Thus, it may, e.g., serve for orienting the external functional device, locking it, and/or transmitting a pressing force to the external functional device, as well as combinations of the above-named functions.

The first contact portion may include a further device for supporting a pressing of the external functional device and/or retaining it such as, e.g., a pressing device and/or a locking device, or be connected to such device.

The first contact portion may be a "coupling surface", an "actuator-sensor plate" (in short: "AS plate"), or a machine interface.

The expression "coupling surface" may refer to, e.g., at least one portion of a top face of a carrier element and/or of a support element and/or of a measurement device or the like of the arrangement and/or of the device.

An "AS plate" may include actuators and/or sensors and/or conduits for coupling to the external functional device or parts thereof.

By means of the coupling surface, which may be—but does not have to be—flat or planar, it is possible to establish an interaction or signal communication between the external functional device and a portion of the device or of the arrangement.

"Actuators" in the presently used sense include—without being restricted thereto—mechanical and/or pneumatic and/or electrical components such as, e.g., valves, positioning and/or regulating members, motor operators, pressure pistons, and the like.

"Sensors" as presently denoted encompass—again without being restricted thereto—electrical, optical, acoustic, virtual and/or digital sensors, transducers and/or probes and the like.

A sensor may qualitatively or quantitatively detect particular physical and/or chemical properties and/or a change thereof, such as an increase or a decrease of an effect, of a characteristic, quality and the like such as, e.g., temperature, pressure, humidity, optical signals such as, e.g., brightness and/or an optical change of a composition, heat radiation, sound, flow rates, and/or the material quality of its environment.

Such sensors may be configured as passive sensors or active sensors.

Conduits as may be employed in accordance with the present invention may include—without being restricted thereto—fluid conduits such as, e.g., blood-conducting passages, substitute conduits, electrical lines, lines for signal communication such as, e.g., glass fiber cables, and the like.

The "second contact portion" of the reception device may be configured like the first contact portion and preferably have the same functions.

The "second contact portion" may be a pressing plate. It may be configured in a flat, stepped, wavy or some other shape. It may get in contact with the external functional device in form of a dot-shaped or a surface contact. It may include a portion corresponding in its geometry to an extension of the external functional device to be coupled, either in the coupled or non-coupled condition. This may facilitate or favor its reception and/or orientation.

The second contact portion may be configured so as to be mobile or rigid.

The second contact portion may be provided so as to get in contact with the external functional device indirectly or directly.

The second contact portion may be a door or a lid for closing an interior of the device of the present invention or of the arrangement or a respective portion thereof.

In a preferred embodiment of the present invention, the device includes at least one peripheral supporting device. The first contact portion may be mounted in an interior of the supporting device.

A like "supporting device" may be a stable supporting device such as, e.g., a support frame. It may be part of the reception device for receiving the at least one external functional device.

The supporting device may be connected to the arrangement through frictional and/or form closure and/or material connections.

The supporting device may be connected to the first and/or the second contact portion.

In particular, when configured as an AS plate, the first contact portion may be disposed in a direction toward the second contact portion and/or the external functional device at a surface of a portion or interior enclosed by the supporting device.

The first contact portion may be disposed in the interior of the supporting device such that a surface of the first contact portion and a surface of the supporting device are situated planarly. In particular, the surface of the first contact portion oriented in the direction of the second contact portion and/or of the external functional device and the surface of the supporting device oriented in the direction of the second contact portion and/or of the external functional device may be situated planarly.

Between the first contact portion disposed in the interior of the supporting device and the supporting device an opening or a free space may be present. Such an opening may form a gap, in particular a peripheral one.

The first contact portion may be mounted in the interior of the supporting device so as to be movable. The first contact portion may be disposed so as to allow it to oscillate, in particular along an axis perpendicular to its surface.

In a further preferred embodiment, at least one of the two contact portions is mounted so as to allow a rotation about at least one axis of rotation. The possibility of rotation or oscillation thereby achieved should be understood as forms of movability within the meaning of the present invention.

An axis of rotation or axis as mentioned in the following has also to be understood as a plurality of axes whenever a person skilled in the art approves this as to be technically feasible. Rotational or oscillating movements that are possible in more than one axial direction at the same time shall in the following also be subsumed as being performed in one axial direction for facilitated reading. This is, however, not intended to restrict the present invention.

Such axis of rotation may be a "physical" axis of rotation. A physical axis of rotation within the meaning of the present invention may be a corporeal axis. It may be a three-dimensionally rigid axis formed by connecting at least one contact portion to the supporting device. It may be oriented horizontal or vertical relative to a typical orientation of the arrangement during use of the arrangement, or relative to the center of the Earth.

A physical axis may be configured as a fixed axis or as a rotating shaft. Preferably it includes at least one suitable bearing. It may respectively be configured by a mounting connection of the first contact portion and/or of the second contact portion to the supporting device and/or some other component part of the arrangement.

Examples of such mounting connections encompass, without being restricted thereto, bearing pins that are introduced and/or inserted into suitable mounting reception device, ball bearings, roller bearings, antifriction bearings, slide bearings, and the like.

Alternatively, an "axis" may in accordance with the present invention also be understood as to be an axis in a three-dimensional space or an axis in one direction in space.

Thus, in this case, it is virtual and not tangible as compared with the corporeal axis explained in the foregoing.

The axis within the meaning of the present invention may be understood as to be a center or a center point of rotation about which the contact portion may be rotated and thus moved. Movability of the contact portion about the axis may enable an oscillating movement of the external functional device upon its being connected to the arrangement or to the device.

In every embodiment, the axis may pass through the contact portion. The axis may, however, also extend externally thereof.

In a connected condition of the external functional device, the axis may pass through the interior of the device and/or through the interior of the arrangement.

The axis may preferably extend such as to allow a rotating or oscillating movement about it solely by a rotation or oscillation of the respective contact portion, however not of further component parts of the device or arrangement. Preferably, this is in particular possible when the rotatable contact portion is the coupling surface for the external functional device, or the so-called machine interface.

The axis may be disposed such as to allow compensatory movements at least of a contact portion for compensating tolerances, deficiencies of form-fit, phenomena of wear etc., but, however, no further rotary movements of a component will be allowed.

In a preferred embodiment, at least one of the two contact portions is mounted at least with the aid of a ball-and-socket joint.

A contact portion mounted with the aid of a ball-and-socket joint may be movable in all directions of space. For example, the first contact portion may be mounted in this way to be rotatable in all directions of space.

In a further preferred embodiment, both of at least the first and the second contact portion have axes of rotation. In a preferred manner, their axes of rotation (all or just some of them) are arranged in parallel to each other. The two axes of rotation may independently be realized as a tangible, corporeal, solid or virtual axis of rotation. They may be configured in the same manner or different from each other.

In a further preferred embodiment, it is intended that at least one contact surface of the first and/or of the second contact portion and at least one contact surface of the external functional device are disposed such that they come to lie on each other in a planar or substantially planar manner in a coupled condition of the external functional device.

In accordance with the present invention, a "contact surface" of the first and/or of the second contact portion and a contact surface of the external functional device designate those surfaces of the respective contact portions and of the external functional device facing each other in the condition of the external functional device being coupled to the arrangement.

The expression "planar", as it should be understood in accordance with the present invention, is to designate the planar or substantially planar contact of the contact portions with the external functional device. In the connected condition, the first and the second contact portions may have a relative orientation such that their respective facing surfaces are parallel or substantially parallel.

In this way, it may advantageously be possible to avoid possible jamming of the contact portions and of the external functional device during the coupling operation. An optimum functional coupling of the components of the external functional device may thus advantageously be ensured. Excessive material strains may advantageously be avoided.

In accordance with the present invention, a "coupled condition" of the external functional device, just like a "connected condition", designates a condition in which the external functional device is functionally connected to the arrangement in its condition of use. Such a condition may be intended for performing a function such as, e.g., a treatment of medical fluids, such as a blood treatment.

In another preferred embodiment, the device of the present invention includes at least one pressing device for pressing the external functional device between the first contact portion and the second contact portion.

A "pressing device" for use in the present invention may be or may include a pressing actuator, an electrical pressing device, a motor actuator, a pneumatic pressing device, a valve, a piston, and the like or combinations thereof.

The pressing device may be connected to the supporting device and/or to the first contact portion and/or to the second contact portion and/or to another component part of the device and/or of the arrangement. It may be connected frictionally and/or positively to at least one of the components mentioned in the foregoing.

The pressing device may apply and/or transmit a pressing force for pressing the external functional device between the contact portions. Such "pressing force" may be a pneumatic force, an electromotive force, magnetic force, inductive force, and the like.

The pressing device may be adapted for maintaining the pressed condition of the external functional device between the two contact portions over a time period. It may include corresponding devices for maintaining, controlling or regulating the pressing force.

The pressing device may be configured so as to ensure the sealed condition of the external functional device through correct placement thereof on one of the contact portions having, for instance, the form of a coupling plane or machine interface.

In another preferred embodiment, the device may further include at least one locking device for fixation of the pressed condition of the external functional device between the first contact portion and the second contact portion.

A "locking device" within the meaning of the present invention may be a bolt, a lock, a catch, a shackle, a plug-type connection, a latching device, and the like.

The locking device may apply an additional force that is required for pressing and may increase a total pressing force. It may include a corresponding device therefore. In this way, the functional coupling of the external functional device between the first contact portion and the second contact portion may advantageously be further ensured.

The locking device may be connected to the supporting device. The pressing device may press the second contact portion via the locking device against the first contact portion.

In a further preferred embodiment, the locking device includes at least one first detection device for detecting a position and/or a condition of the first contact portion and/or of the second contact portion.

A "detection device" as may presently be employed may be, for instance, a sensor and/or a detector which recognizes a position and/or a condition of the first contact portion and/or of the second contact portion, and optionally evaluates them.

A "position and/or a condition" of the first contact portion and/or of the second contact portion may denote a geometrical arrangement and/or orientation of the first contact portion and/or of the second contact portion. It may denote an arrangement of the first contact portion and of the second contact portion relative to each other.

The detection device and/or the device and/or the arrangement may include device for evaluating and/or controlling and/or regulating, in particular correcting, the position and/or condition of the first contact portion and/or of the second contact portion. Such device may be in signal communication with each other.

The locking device may include a suitable sensor arrangement for recognizing the conditions of the second contact portion such as, e.g., a condition "door closed" and/or "door locked." In accordance with the present invention, a display device and/or an alarm device for communicating the recognized condition may be provided.

In another preferred embodiment, the first contact portion and/or the second contact portion are connected to the supporting device, the device or the arrangement via an articulation.

An "articulation" as may be used in accordance with the present invention may denote a stable articulation such as, e.g., a hinge, a door hinge, a lever and the like.

A door hinge preferably is configured to have one axis.

The contact portion that is connected to the supporting device by such an articulation may preferably be rotatable about an axis extending, e.g., in a vertical direction. It may be adapted to be opened and closed particularly in the form of a door and/or cover.

In a yet further preferred embodiment, at least one of the contact portions or a contact surface or a pressing surface thereof is connected to the device or to the arrangement in a rotatable or pivotable manner—for example by using a door or as a part of a door. Here, the axis of rotation—e.g. in the form of an axis of rotation of a door hinge of the door—is situated in one plane with and preferably moreover in parallel with an axis of rotation of another contact portion that is mounted rotatably in this embodiment.

In a further preferred embodiment, the first contact portion and/or the second contact portion and/or the articulation include at least one device for receiving linking elements for functionally linking the external functional device to the arrangement.

Such a "device for receiving linking elements" may be an opening, in particular an opening extending through the component, such as, e.g., a leadthrough. In its interior it may be configured for receiving conduits, guide elements, tensile elements, or the like.

"Linking elements" as considered in the scope of the present invention may encompass conduits, such as electrical and/or pneumatic conduits, cables such as glass fiber cables, fluid conduits and the like.

Such linking elements may supply the external functional device with pressure, for instance. Through their intermediary, sensors may moreover also be coupled to the external functional device.

In a further preferred embodiment, the first contact portion and/or the second contact portion include at least one transparent portion.

The expression "transparent" as used in the present invention denotes a component configured to be translucent, in particular to the human eye.

Without being restricted thereto, a "transparent portion" may be formed of glass, translucent plastics, translucent film or the like, or encompass the like.

A transparent portion may advantageously admit observation and/or optical monitoring of an interior of the arrangement. It may be opaque.

A contact portion, for example the second contact portion, in particular when configured in the form of a door, may include a stable support structure having a transparent cover provided in partial areas. Such an embodiment may advantageously allow a user of the arrangement to optically monitor areas of interest of the external functional device from the outside.

In a further preferred embodiment, the first contact portion and/or the second contact portion may include at least one positioning device for positioning the external functional device within the device.

A "positioning device" within the meaning of the present invention may be configured for receiving in a defined manner and/or positioning three-dimensionally and/or frictional fastening and/or fastening by form closure the external functional device to the contact portion. It may, e.g., be configured as a positioning pin, positioning mandrel and the like.

The external functional device may include at least one device for receiving the positioning device such as, e.g., an opening, in particular a through hole.

Positioning of the external functional device within the device may be effected with the aid of suitable device, e.g., in accordance with the so-called hole/oblong hole principle.

In a further preferred embodiment, the device includes at least one sealing device.

Such a "sealing device" may be suitable for sealing a first volume of the device against a second volume of the device.

Such a sealing device may be a mat. It may be a rubber mat. It may be configured as a multi-component sealing device. It may include at least one elastomer material. It may be disposed between the first contact portion and the second contact portion. During the use of the external functional device or for the connected condition, respectively, it may be provided between a movable contact portion and the external functional device.

The sealing device may include sensors and/or actuators and/or conduits and/or parts thereof and/or be adapted for receiving them. The sealing device may be configured to be integrated with such components. The components may be connected with the sealing device by form closure and/or frictional and/or material connections.

Suitable sealing device include those that are disclosed in one of the patent specifications DE 10 2007 042 964, DE 10 2008 062 037, or in the patent application the applicant of the present invention has filed at the German Patent and Trademark Office with the title "Abdichtungseinrichtung zum Abdichten eines Volumens einer medizinischen Behandlungsanordnung gegen ein weiteres Volumen sowie Anordnung and Verfahren" [A sealing device for sealing a volume of a medical treatment arrangement against another volume, as well as an arrangement and a method], which was deposited as DE 10 2009 012 632.5 on the same application date as the present application. The relevant disclosure of the named patent applications is herewith fully incorporated by way of reference.

A method of the present invention includes connecting at least one external functional device to the arrangement by using the device of the present invention.

An object of the present invention is also achieved by an arrangement that includes at least one device of the present invention. In a preferred embodiment, the arrangement of the present invention is a blood treatment apparatus, in particular a dialysis apparatus, a hemodialysis apparatus, a hemodiafiltration apparatus or the like.

In order to avoid repetitions, reference is now expressly made to the embodiments described in the foregoing, which unrestrictedly apply to any embodiments of the method of the present invention and of the arrangement of the present invention. In addition, the named advantages may be obtained undiminished.

The device of the present invention is advantageously suited for accurate coupling an external functional device to an arrangement. Due to the at least one contact portion configured, e.g., to be movable in a direction of rotation, a compensation of tolerances occurring between the single component parts may be possible and an optimum mechanical and/or functional coupling may be ensured. By using the device of the present invention, complex coupling operations as described, e.g., in the patent application having publication No. DE 10 2007 04 29 64, the relevant disclosure of which is in turn fully incorporated by way of reference, are advantageously possible in a simple, quick and error-free manner.

Secure and leakage-free coupling in combination with, for instance, the demand of a high pressure homogeneously distributed across the contact surfaces—which is generally made difficult by manufacturing tolerances, elastic material properties and wear of the single components in the course of their service life—may advantageously be ensured by the mobility and resilience, or automatic adjustment, of a contact portion in at least one direction of space.

Due to the possibility of automatic adaptation of a contact portion, it may advantageously be possible to ensure a suitable, secure and error-free as well as low-wear coupling of the sensors and actuators of the coupling surface—also referred to as machine interface—and thus the desired function thereof with respect to their coupling mates of the external functional device and vice versa.

As all the essential components may be mounted and positioned on a single stable supporting device, accurate pressing of the component parts by relatively high forces may advantageously be achieved.

Due to the mobility or rotatability of the contact portion about an axis, a pressing force may advantageously be distributed homogeneously to a surface or to several points. Where necessary, it is thus advantageously also possible to apply comparatively high forces. Mobility or rotatability about an axis may ensure that an application of pressure will not result in inadmissible stress peaks.

This particularly applies as the contact surfaces may advantageously always be oriented in parallel to each other due to the arrangement of at least one contact portion, preferably two contact portions, so as to be rotatable about an axis as provided in accordance with the present invention. This in turn allows for optimum coupling of the at least one external functional device while avoiding stress peaks. In addition, a particularly accurate mechanism may be enabled whereby the contact portions for connecting the external functional device to the device or to the arrangement are guided toward each other.

By appropriately arranging mounting points of the first and second contact portions, it may moreover advantageously be possible to compensate a flexure of the components that is caused by the pressing force for coupling the external functional device.

The possible mobility or oscillating movement of a contact portion may compensate manufacturing tolerances of the single components, of the first and/or second contact portions, of the sealing device, and advantageously reduce or substantially avoid wear thereof.

BRIEF DESCRIPTION OF THE DRAWINGS

In the following, the device of the present invention shall be described by way of a preferred embodiment thereof while making reference to FIGS. 1 to 3. In the drawing, same reference numerals designate same or identical elements, wherein.

DETAILED DESCRIPTION OF THE DRAWINGS

Figure 1:
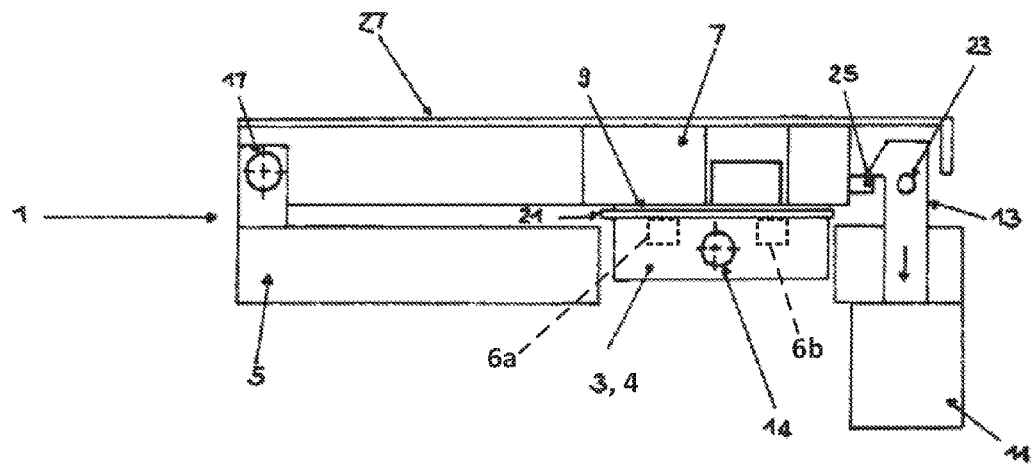
FIG. 1 shows a schematic lateral view of the device of the present invention in accordance with the preferred embodiment in cross-section.

FIG. 1 schematically shows a lateral view of a device 1 of the present invention in sectional representation. The device 1 includes a first contact portion 3 in the form of an AS plate 4 which is mounted for vertical oscillation or rotation in a supporting device 5, which is here configured as a stable, peripheral support frame. The AS plate 4 includes actuators 6*a*-*b*, and/or sensors 6*a*-*b*, and/or conduits 6*a*-*b*, for coupling to an external functional device 9 or parts thereof.

On the supporting device 5 a second contact portion 7, here a stable or robust door, is fastened by means of an articulation 17. The second contact portion 7 serves for covering and clamping an external functional device 9 here having the form of a blood-conducting disposable cassette.

In order to additionally support damping and/or pressing of the external functional device 9, a pressing device 11, in the present case a pressing actuator, is arranged which is fastened to the supporting device 5. The pressing device 11 may be adapted to press the door as a second contact portion 7 via a locking device 13, here a bolt, against the AS plate 4 as a first contact portion 3. A magnet 25 for retaining the door, especially in a condition without an inserted external functional device 9, is disposed between the bolt as a locking device 13 and the disposable cassette as an external functional device 9.

Figure 2:
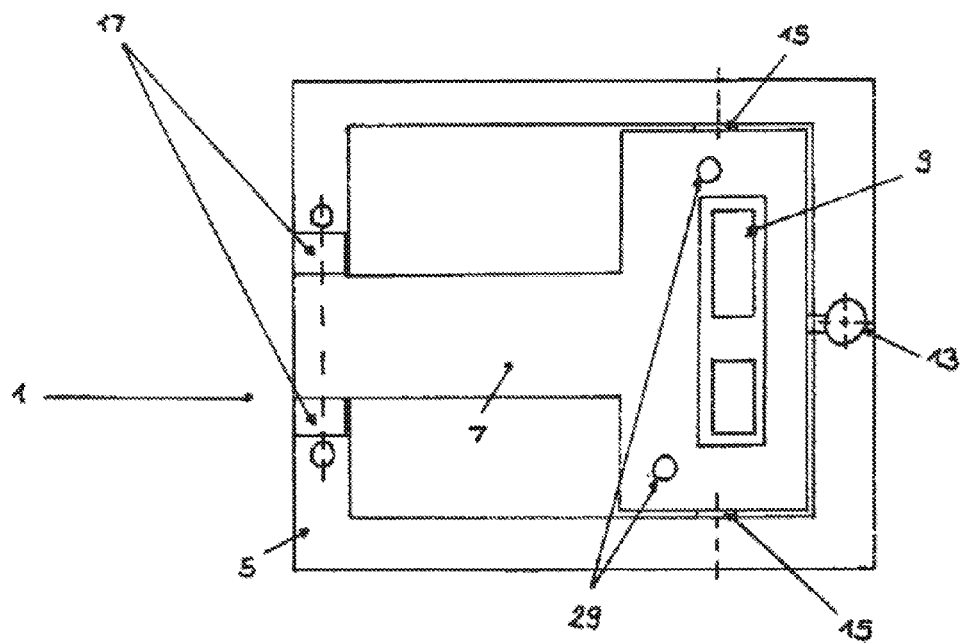
FIG. 2 shows a schematic front view of the device of the present invention of FIG. 1.

The first contact portion 3 is mounted in the supporting device 5 by means of an axis or a shaft 14 at two mounting points 15 at its narrow side (its top and bottom sides in FIG. 2).

The articulation 17 and the locking device 13 of the second contact portion 7 are each centrally attached to the supporting device 5 and connect the second contact portion 7 to the supporting device 5.

The locking device 13 includes an integrated sensor as a detection device 23. The sensor may, for example, detect whether the door, being the second contact portion 7, is closed.

Above or in front of the door a door cover 27 is attached. The door cover 27 may include transparent areas.

FIG. 2 shows a front view of the device of the present invention of FIG. 1 without the door cover 27. The door includes linking elements 29 for supplying the disposable cassette with pressure.

Figure 3:
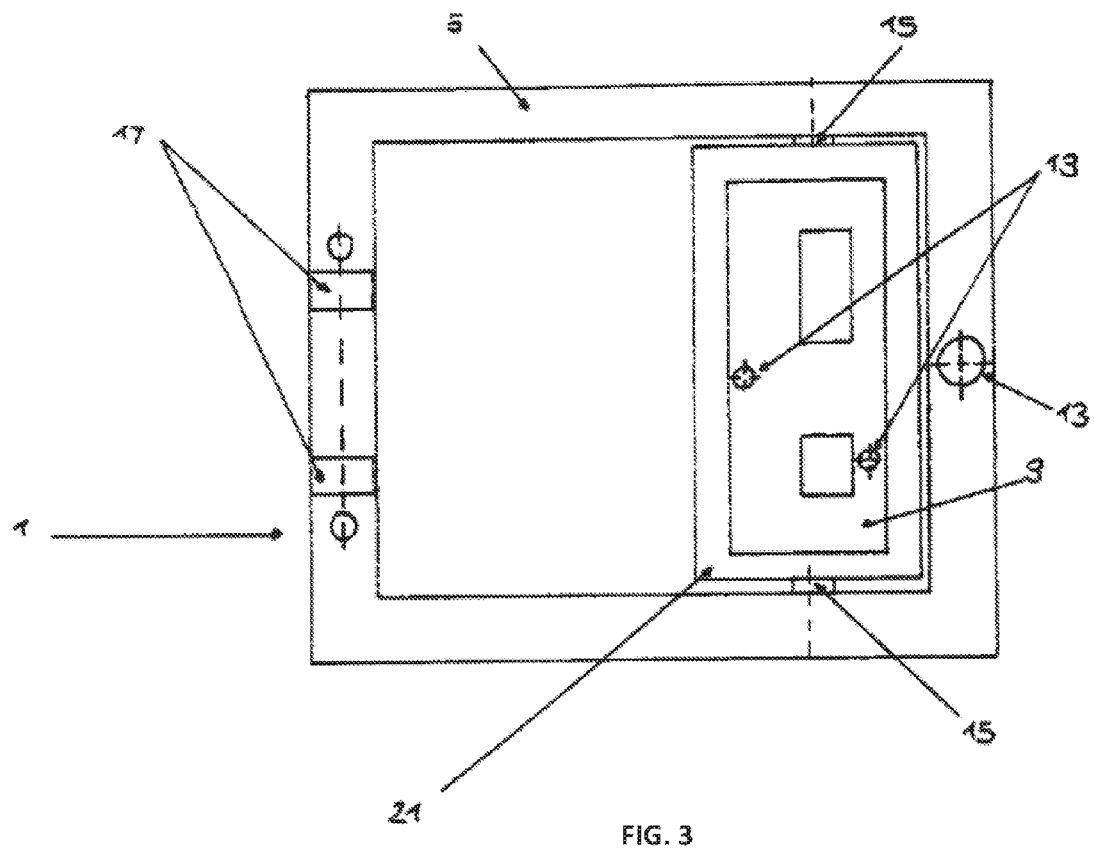
FIG. 3 shows another schematic front view of the device of the present invention of FIGS. 1 and 2.

FIG. 3 shows the device of the present invention of FIG. 1 without the door and without the door cover 27.

In FIG. 3, a mat is furthermore disposed as a sealing device 21 below the disposable cassette on the AS plate (the latter is not visible in FIG. 3 as it is covered by the disposable cassette and the mat).

In FIG. 3, openings 19 for receiving fastening device such as, e.g., positioning mandrels (not shown) are represented. Such positioning mandrels may be suitable for fixation of the external functional device at the first contact portion in accordance with the hole/oblong hole principle.

The present invention is not restricted to the embodiment described in the foregoing which merely serves for illustrative purposes.

The invention claimed is:

1. A device for connecting a multi-functional disposable cassette to an extracorporeal blood treatment apparatus, wherein the device comprises:
   at least one receptacle having at least one first contact portion and at least one second contact portion for receiving the multi-functional disposable cassette between the first contact portion and the second contact portion, wherein the first contact portion and the second contact portion are rotatably mounted about differing axes of rotation,
   wherein one of the at least one first or second contact portions comprises at least one actuator-sensor plate,
   wherein the at least one actuator-sensor plate comprises at least two actuators and at least two sensors, and wherein each actuator and each sensor is configured to couple to and interact with the multi-functional disposable cassette while the multi-functional disposable cassette is between the first contact portion and the second contact portion.

2. The device according to claim 1, further comprising at least one peripheral support, wherein the first contact portion is mounted in an interior of the support.

3. The device according to claim 2, wherein the first contact portion, the second contact portion, or both is connected to the support by an articulation.

4. The device according to claim 1, further comprising one or more positioning devices on at least one of the first contact portion and the second contact portion, the one or more positioning devices defining a position at which the multi-functional disposable cassette is received relative to the at least one of the first contact portion and the second contact portion.

5. The device according to claim 4, wherein an axis of rotation of the first contact portion and an axis of rotation of the second contact portion are disposed parallel with each other.

6. The device according to claim 1, wherein an axis of rotation of the first contact portion and an axis of rotation of the second contact portion are disposed parallel with each other.

7. The device according to claim 1, wherein at least one contact surface of the first contact portion, of the second contact portion, or both and at least one contact surface of the multi-functional disposable cassette are adapted to lie on each other in a planar manner when the external functional device is received within the receptacle.

8. The device according to claim 1, further comprising at least one pressing device for pressing the second contact portion toward the first contact portion.

9. The device according to claim 8, wherein the pressing device is chosen from the group consisting of:
   a pressing actuator, an electrical pressing device, a motor actuator, a pneumatic pressing device, a valve, a piston, and combinations thereof.

10. The device according to claim 1, further comprising at least one locking device for fixation of a pressed condition of the multi-functional disposable cassette between the first contact portion and the second contact portion.

11. The device according to claim 10, wherein the locking device includes at least one sensor device for detecting a position, a condition, or both of the first contact portion, of the second contact portion, or of both.

12. The device according to claim 1, wherein the first contact portion, the second contact portion, an articulation, or any combination thereof includes at least one opening for receiving linking elements for functionally linking the multi-functional disposable cassette to the extracorporeal blood treatment apparatus.

13. The device according to claim 1, wherein the first contact portion, the second contact portion, or both includes at least one transparent portion.

14. The device according to claim 1, wherein the first contact portion includes the actuator-sensor plate and at least one positioning device for positioning the multi-functional disposable cassette inside the device.

15. The device according to claim 1, further comprising at least one sealing device disposed between at least the first contact portion and the second contact portion.

16. The device according to claim 1, wherein the multi-functional disposable cassette is a blood-conducting cassette.

17. The device according to claim 1, wherein said first contact portion comprises the at least one actuator-sensor plate and the second contact portion comprises a door or a lid.

18. The device according to claim 1, wherein at least one of the first contact portion and the second contact portion is configured to oscillate in at least two directions.

19. An extracorporeal blood treatment apparatus, comprising:
   at least one receptacle having at least one first contact portion and at least one second contact portion for receiving a multi-functional disposable cassette between the first contact portion and the second contact portion, wherein the first contact portion and the second contact portion are rotatably mounted about differing axes of rotation
   wherein one of the at least one first or second contact portions comprises at least one actuator-sensor plate,
   wherein the at least one actuator-sensor plate comprises at least two actuators and at least two sensors, and wherein each actuator and each sensor is configured to couple to and interact with the multi-functional disposable cassette while the multi-functional disposable cassette is between the first contact portion and the second contact portion, and
   wherein the extracorporeal blood treatment apparatus is a dialysis apparatus, a hemodialysis apparatus, a hemofiltration apparatus, or a hemodiafiltration apparatus.

* * * * *